US00PP20711P2

(12) United States Plant Patent
Meilland

(10) Patent No.: US PP20,711 P2
(45) Date of Patent: Feb. 2, 2010

(54) GRANDIFLORA ROSE PLANT NAMED 'MEIROYLEAR'

(50) Latin Name: *Rosa hybridal*
Varietal Denomination: Meiroylear

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/314,187

(22) Filed: Dec. 5, 2008

(51) Int. Cl.
*A01H 5/00* (2006.01)

(52) U.S. Cl. ..... Plt./132
(58) Field of Classification Search ..... Plt./132
See application file for complete search history.

*Primary Examiner*—Kent L Bell
(74) *Attorney, Agent, or Firm*—Buchanan Ingersoll & Rooney PC

(57) ABSTRACT

A new and distinct variety of Grandiflora rose plant is provided that forms on a recurrent basis attractive double blossoms that are bright red with yellow stripes finishing to medium pink and cream. The vegetation is vigorous and a bushy upright growth habit is displayed. Susceptibility to Black Spot has been observed during observations to date. The plant is particularly well suited for providing distinctive attractive ornamentation in the landscape.

1 Drawing Sheet

Figure 1:
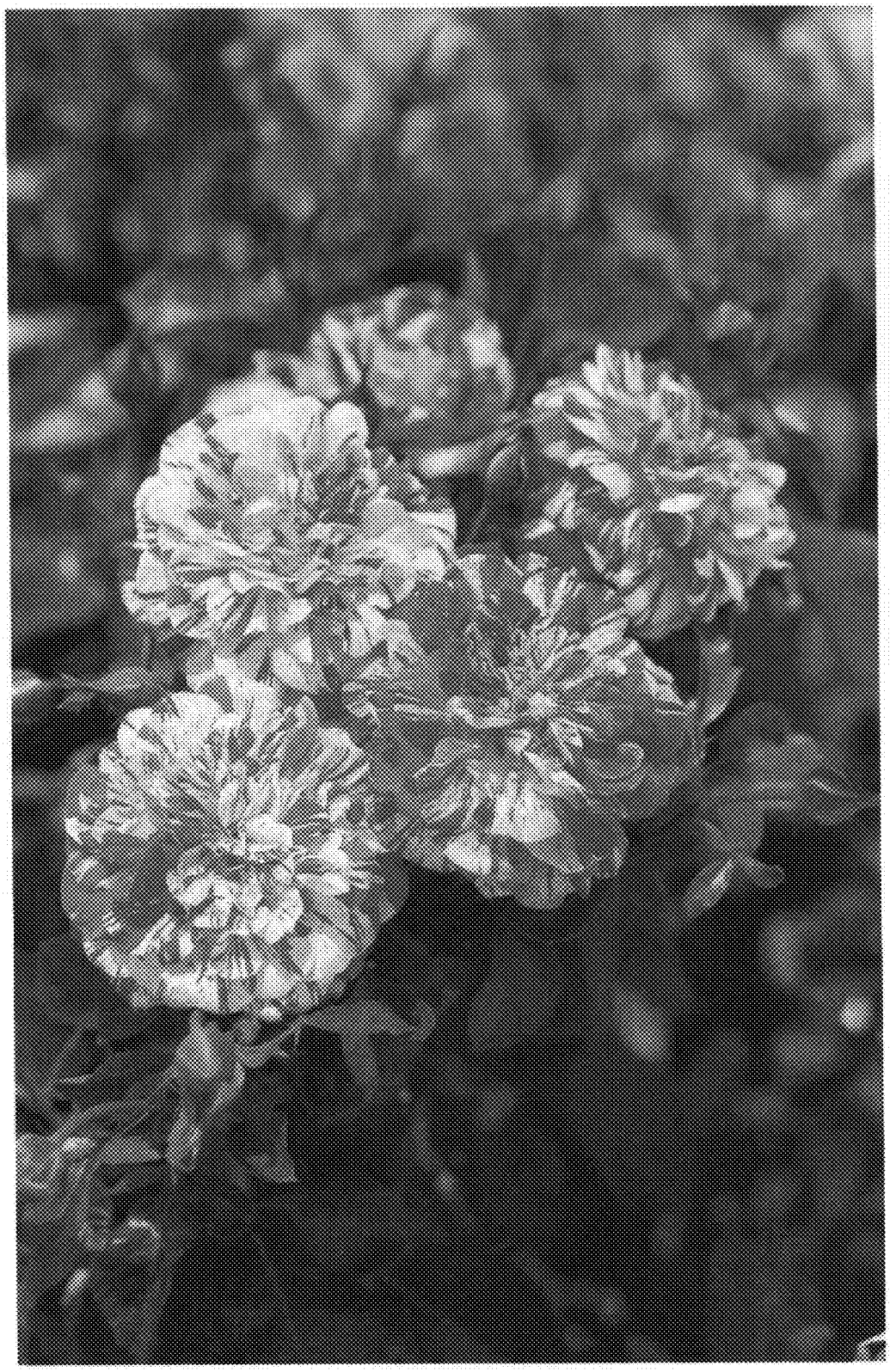

Botanical/commercial classification: *Rosa hybrida*/Grandiflora Rose Plant.

Varietal denomination: cv. Meiroylear.

SUMMARY OF THE INVENTION

The new variety of *Rosa hybrida* Grandiflora rose plant was created in France during May 1997 by artificial pollination wherein two parents were crossed which previously had been studied in the hope that they would contribute the desired characteristics. The female parent (i.e., the seed parent) was the product of the cross of the 'Meipsilon' variety (non-patented in the United States) and the 'Meivestal' variety (non-patented in the United States). The male parent (i.e., the pollen parent) was the 'Wekplapep' variety (U.S. Plant Pat. No. 10,126). This 'Meipsilon' variety is marketed under the YAKIMOUR trademark. The 'Meivestal' variety is marketed under the SENATOR BURDA trademark. The 'Wekplapep' variety is marketed under the SENTMENTAL trademark. The parentage of the new variety can be summarized as follows:

('Meipsilon'×'Meivestal')×'Wekplapep'.

The seeds resulting from the above pollination were sown and small plants were obtained which were physically and biologically different from each other. Selective study during June 2001 resulted in the identification of a single plant of the new variety.

It was found that the new Grandiflora rose plant of the present invention:

(a) forms vigorous vegetation,
(b) forms a bushy upright growth habit,
(c) abundantly and substantially continuously forms attractive double blossoms that are bright red with yellow stripes finishing to medium pink and cream,
(d) displays attractive glossy medium green foliage, and
(e) is particularly well suited for providing distinctive attractive ornamentation in the landscape.

The new variety well meets the needs of the horticultural industry and can be grown to advantage in parks and gardens.

The new variety can be readily distinguished from its ancestors. For instance, 'Meipsilon' variety is a Hybrid Tea that forms blossoms which display a red blend coloration. The 'Meivestal' variety is a Hybrid Tea which forms brilliant currant red blossoms having an intense fragrance. The 'Wekplapep' variety is a Floribunda which forms intensely fragrant blossoms having a red blend coloration.

Additionally, the new variety can be readily distinguished from the 'Meisiastri' variety (U.S. Plant patent application Ser. No. 12/314,185 filed concurrently herewith). Unlike the new variety of the present invention, the 'Meisiastri' variety is a Floribunda that forms striped red and pink blossoms.

The new variety has been found to undergo asexual propagation at Wasco, Calif., U.S.A., by a number of routes, including budding, grafting, and the use of cuttings. Such asexual propagation by the above-mentioned techniques has shown that the characteristics of the new variety are stable and are strictly transmissible by such asexual propagation from one generation to another. Accordingly, the new variety undergoes asexual propagation in a true-to-type manner.

The new variety has been named 'Meiroylear', and is being marketed under the ALL AMERICAN MAGIC trademark.

BRIEF DESCRIPTION OF THE PHOTOGRAPH

The accompanying photograph shows as nearly true as it is reasonably possible to make the same, in a color illustration of this character, a typical specimen of the new variety. Blossoms in various stages of development as well as foliage are illustrated. The illustrated plant was approximately two years of age, and was being grown outdoors at Wasco, Calif., U.S.A.

DETAILED DESCRIPTION

The chart used in the identification of the colors is that of The Royal Horticultural Society (R.H.S. Colour Chart) except where ordinary color terms are utilized. Such common color terms are to be accorded their customary dictionary significance. The description is based upon the observation of plants of the new variety at an age of approximately five years during the month of August while being grown near West Grove, Pa., U.S.A.

Class: Grandiflora.

Plant:

*Growth habit.*—Vigorous, bushy and upright.

*Blooming habit.*—Abundant and substantially continuous.

*Height.*—Commonly approximately 5.5 feet at an age of two years.

*Width.*—Commonly approximately 3.5 feet at an age of two years.

Branches:

*Color.*—Young stems: commonly near Yellow-Green Group 146B. adult wood: commonly near Yellow-Green Group 146C.

*Thorns.*—Size: commonly approximately 1 cm in length, approximately 6 mm in size at the base, and less than 1 mm in size at the apex. color: commonly near Greyed-Yellow Group 161A.

Leaves:

*Overall appearance.*—Attractive medium green glossy foliage.

*Leaflets.*—Shape: generally oval. number 3, 5 and 7. apex: acuminate. base: aequilateral. size: the terminal leaflets commonly are approximately 4.5 cm in length on average and approximately 3 cm in width on average, and the lower leaflets commonly are approximately 2 cm in length on average and approximately 1.3 cm in width on average. serration: small and single. texture: smooth and glossy on the upper surface, and scabrous on the under surface. color (young foliage): Green Group 137A on the upper surface, and Yellow-Green Group 144A on the under surface. color (adult foliage): Yellow-Green Group 146A on the upper surface, and Yellow-Green Group 145B with some Greyed-Red Group 179A on the edges and veins on the under surface.

Inflorescence:

*Number of flowers.*—Commonly approximately 5 double blossoms per stem in a cluster.

*Peduncle.*—Moderately strong, commonly approximately 3 cm in length on average, approximately 3 mm in diameter on average, and near Yellow-Green Group 145A in coloration with some Greyed-Orange Group 176C on the side exposed to the sun.

*Sepals.*—Texture: smooth on both surfaces and glaucous on the upper surface. size: approximately 2.5 cm in length, and approximately 0.5 cm in width at the base. color: near Green Group 138B on the upper and under surfaces.

*Buds.*—Shape: oval. length: approximately 2.2 cm on average. width: approximately 1.5 cm at the widest point on average.

*Flower.*—Diameter approximately 5 cm on average. color (when fully open): upper side: Red Group 53C with stripes of Yellow-White Group 158A, and with Yellow Group 6C at the point of attachment. Some petals commonly exhibit more striping than others, some are almost entirely Red Group 53C, and others are almost entirely Yellow-White Group 158A. under side: nearly consistently Yellow Group 3C at the point of attachment and thereafter blending to near Red Group 36D. color stability: with full maturity the bright red of the blossoms tends to turn to pink, and the yellow stripes of the blossoms tend to assume a more cream coloration. fragrance: very light and sweet. petal number approximately 66 on average under normal growing conditions. petal drop: good with the petals commonly detaching cleanly before drying. stamen number approximately 30 on average. anthers: regularly arranged around the styles. filaments: commonly approximately 0.5 to 1 cm in length on average, and near Yellow Group 5C in coloration. pistils: separate and free, and approximately 27 on average. styles: commonly near Red Group 45B in coloration. stigmas: commonly near Yellow Group 13C in coloration. hips: none available for inspection.

Development:

*Vegetation.*—Vigorous and strong.

*Blooming.*—Abundant and substantially continuous.

*Tolerance to diseases.*—Is susceptible to Black Spot during observations to date.

I claim:

1. A new and distinct Grandiflora rose plant characterized by the following characteristics:

(a) forms vigorous vegetation, (b) forms a bushy upright growth habit, (c) abundantly and substantially continuously forms attractive double blossoms that are bright red with yellow stripes finishing to medium pink and cream, (d) displays attractive glossy medium green foliage, and (e) is particularly well suited for providing attractive distinctive ornamentation in the landscape;

substantially as shown and described.

* * * * *